United States Patent [19]

Moore et al.

[11] Patent Number: 5,652,117
[45] Date of Patent: Jul. 29, 1997

[54] HUMAN TRANSCRIPTION FACTOR IIA

[75] Inventors: Paul A. Moore, Germantown; Craig A. Rosen, Laytonsville, both of Md.

[73] Assignee: Human Genome Sciences, Inc., Rockville, Md.

[21] Appl. No.: 411,635

[22] PCT Filed: Sep. 20, 1994

[86] PCT No.: PCT/US94/10644

§ 371 Date: Apr. 11, 1995

§ 102(e) Date: Apr. 11, 1995

[87] PCT Pub. No.: WO96/09311

PCT Pub. Date: Mar. 28, 1996

[51] Int. Cl.$^6$ .......................... C07H 21/04; C07K 14/435; C12N 15/00

[52] U.S. Cl. .................. 435/69.1; 435/320.1; 435/91.41; 435/348; 435/365; 435/358; 435/366; 435/419; 530/350; 536/23.5

[58] Field of Search ............................. 536/23.5; 435/29, 435/69.1, 240.2, 320.1; 530/350, 387.1; 424/172.1; 514/2, 44

[56] References Cited

PUBLICATIONS

Ranish et al., "Isolation of Two Genes That Encode Subunits of the Yeast Transcription Factor IIA", Science, vol. 255, pp. 1127–1129. Feb. 28, 1992.

Cortes et al., "Factors Involved in Specific Transcription by Mammalian RNA Polymerase II: Purification and Analysis of Transcription Factor IIA and Identification of Transcription Factor IIJ", Molecular and Cellular Biology, vol. 12, No. 1, p. 4 Jan. 1992.

Buratowski et al., "Five Intermediate Complexes in Transcription Initiation by RNA Polymerase II", Cell, vol. 56, No. 4, pp. 549–561. Feb. 24, 1989.

PCT International Search Report.

Buratowski, *Cell*, Apr. 8, 1944, vol. 77, pp. 1–3.

Buratowski, et al., *Cell*, pp. 549–561.

Gould, et al., *Proc. Nat'l Acad. Sci.*, Mar. 1989, vol. 86, pp. 1934–1938.

Matsudaira, *The Journal of BioChem*, Jul. 25, 1987, vol. 262, No. 21, pp. 10035–10038.

Lathe, *J. Molec. Biol.*, 1985, vol. 185, pp.1–12.

Tjian et al., *Cell*, Apr. 8, 1994, vol. 77, pp. 5–8.

Ranish, et al., *Science*, Feb. 28, 1992, vol. 255, pp. 1127–1129.

*Primary Examiner*—George C. Elliott
*Assistant Examiner*—Sean McGarry
*Attorney, Agent, or Firm*—Elliot M. Olstein

[57] ABSTRACT

The small (γ) subunit of human Transcription Factor IIA and DNA (RNA) encoding such polypeptide and a procedure for producing such polypeptide by recombinant techniques. Also disclosed are methods for utilizing such polypeptide for regulating gene-specific and global transcription. Antagonists against such polypeptide and their use to inhibit transcription are also disclosed.

24 Claims, 9 Drawing Sheets

FIG. 1A

```
GGCCCCCTCTAGAACTAGTGGATCCCCCGGCCTGCAGGAATTCGGCACGAGCTGGAGAG          60
GTGGTGGGAGAAGTAGGAACCTCCTGCCGGCTCGTGGGCTTCTGTCCGCTCCGGA            120
GGGAAGCGCCTTCCCCACAGGACATCAAGCAAGCTTGAATAAGAAAACAAATTCTTCC          180

M  A  Y  Q  L  Y  R  N  T  T  L  G  N  S  L  Q  E           (17)
TCCTAAGCCATGGCATATCAGTTATACAGAAATACTACTTTGGGAAACAGTCTTCAGGAG         240

S  L  D  E  L  I  Q  S  Q  Q  I  T  P  Q  L  A  L  Q  V  L          (37)
AGCCTAGATGAGCTCATACAGTCTCAACAGATCACCCCCCAACTGCCCTTCAAGTTCTA         300

L  Q  F  D  K  A  I  N  A  A  L  A  Q  R  V  R  N  R  V  N          (57)
CTTCAGTTTGATAAGGCTATAAATGCAGCACTGGCTCAGAGGGTCAGAAACAGAGTCAAT        360

F  R  G  S  L  N  T  Y  R  F  C  D  N  V  W  T  F  V  L  N          (77)
TTCAGGGGCTCTCTAAATACGTACAGATTCTGCGATAATGTGTGGACTTTTGTACTGAAT        420

D  V  E  F  R  E  V  T  E  L  I  K  V  D  K  V  K  I  V  A          (97)
GATGTTGAATTCAGAGAGGTGACAGAACTTATTAAAGTGGATAAAGTGAAAATTGTAGCC        480

C  D  G  K  N  T  G  S  N  T  T  E  *                             (109)
TGTGATGGTAAAAATACTGGCTCCAATACTACAGAATGAATAGAAAAAATATGACTTTTT        540

TACACCATCTTCTGTTATTCATTGCTTTTGAAGAGAAGCATAGAAGAGACTTTTATTTA         600
TCTAGAATTGCAGAAATGACTACACTGTGCTATACCAGAGAATTCCAGTAGAAAGAAAC         660
TTGTAACTCTGTAGCCTCTTACACCTTATTATACAGCATGAAAACCATAACTTTT             720
TTTTAAGGACAAAAGTTGTTGCCTTCCTAAGAACCTTCTTTAATAAACTTCATTTTAAAC        780
TCTGAAAAAAAAAAAAAAAAA  801
```

FIG. 1B

```
Human    1  MA----YQLYRNTTLGNSLQESLDELIQSQQITPQLALQVLLQFDKAINAALAQR   51
            ||    |||  ||:||||| :|||: ||  ||  ||| ||||:  |||
Yeast    1  MAVPGYYELYRRSTIGNSLVDALDTLISDGRIEASLAMRVLETFDKVVAETLKDN   55

Human   52  VRNRVNFRGSLNTYRFCDNVWTF-VLND----VE--FREVTE------LIKVDKV   93
            :: ||||  ||   | |||||| ||:     ||  |  ||:      :! |!::
Yeast   56  TQSKLTVKGNLDTYGFCDDVWTFIVKNCQVTVEDSHRDASQNGSGDSSVISVDKL  111

Human   94  KIVACDGKNTGSNTTE  109
            :|||| |  |
Yeast  112  RIVACNSKKSE      122
```

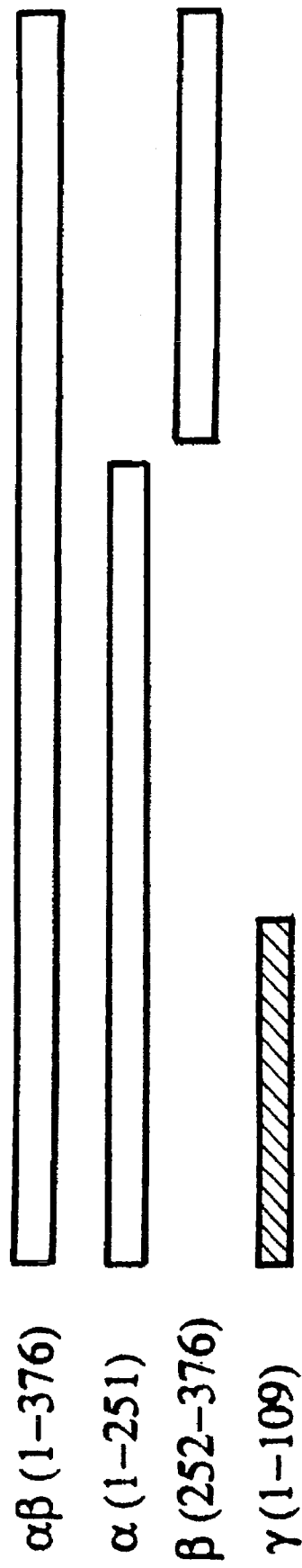

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 804 BASE PAIRS
( B ) TYPE: NUCLEIC ACID
( C ) STRANDEDNESS: SINGLE
( D ) TOPOLOGY: LINEAR ( i i ) MOLECULE TYPE: cDNA ( x i ) SEQUENCE DESCRIPTION: SEQ ID NO:1:

```
GGCCCCTCT  AGAACTAGTG  GATCCCCCG  GCCTGCAGGA  ATTCGGCACG  AGCTGGAGAG      60
```

```
GTGGTCGGAG  AAGTAGGAAC  CTCCTGCCGG  GCTCGTGGCG  GCTTCTGTCC  GCTCCGCGGA   120

GGGAAGCGCC  TTCCCCACAG  GACATCAATG  CAAGCTTGAA  TAAGAAAAAC  AAATTCTTCC   180

TCCTAAGCCA  TGGCATATCA  GTTATACAGA  AATACTACTT  TGGGAAACAG  TCTTCAGGAG   240

AGCCTAGATG  AGCTCATACA  GTCTCAACAG  ATCACCCCCC  AACTTGCCCT  TCAAGTTCTA   300

CTTCAGTTTG  ATAAGGCTAT  AAATGCAGCA  CTGGCTCAGA  GGGTCAGGAA  CAGAGTCAAT   360

TTCAGGGGCT  CTCTAAATAC  GTACAGATTC  TGCGATAATG  TGTGGACTTT  TGTACTGAAT   420

GATGTTGAAT  TCAGAGAGGT  GACAGAACTT  ATTAAAGTGG  ATAAAGTGAA  AATTGTAGCC   480

TGTGATGGTA  AAAATACTGG  CTCCAATACT  ACAGAATGAA  TAGAAAAAAT  ATGACTTTTT   540

TACACCATCT  TCTGTTATTC  ATTGCTTTTG  AAGAGAAGCA  TAGAAGAGAC  TTTTTATTTA   600

TTCTAGAATT  GCAGAAATGA  CTACACTGTG  CTARACCAGA  GAATTCCAGT  AGAAAGAAAC   660

TTGTAACTCT  GTAGCCTCTT  ACATCACCTT  TATTATACAG  CATGAAAAAC  CATAACTTTT   720

TTTTAAGGAC  AAAAGTTGTT  GCCTTCCTAA  GAACCTTCTT  TAATAAACTC  ATTTTAAAAC   780

TCTGAAAAAA  AAAAAAAAA   AAAA                                            804
```

(2) INFORMATION FOR SEQ ID NO:2:

(i) SEQUENCE CHARACTERISTICS:
        (A) LENGTH: 109 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

```
Met  Ala  Tyr  Gln  Leu  Tyr  Arg  Asn  Thr  Thr  Leu  Gly  Asn  Ser  Leu
               5                         10                        15

Gln  Glu  Ser  Leu  Asp  Glu  Leu  Ile  Gln  Ser  Gln  Gln  Ile  Thr  Pro
              20                         25                        30

Gln  Leu  Ala  Leu  Gln  Val  Leu  Leu  Gln  Phe  Asp  Lys  Ala  Ile  Asn
              35                         40                        45

Ala  Ala  Leu  Ala  Gln  Arg  Val  Arg  Asn  Arg  Val  Asn  Phe  Arg  Gly
              50                         55                        60

Ser  Leu  Asn  Thr  Tyr  Arg  Phe  Cys  Asp  Asn  Val  Trp  Thr  Phe  Val
              65                         70                        75

Leu  Asn  Asp  Val  Glu  Phe  Arg  Glu  Val  Thr  Glu  Leu  Ile  Lys  Val
              80                         85                        90

Asp  Lys  Val  Lys  Ile  Val  Ala  Cys  Asp  Gly  Lys  Asn  Thr  Gly  Ser
              95                        100                       105

Asn  Thr  Thr  Glu
              109
```

(2) INFORMATION FOR SEQ ID NO:3:

(i) SEQUENCE CHARACTERISTICS:
        (A) LENGTH: 29 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

```
GCGGCGGATC  CATGGCATAT  CAGGTATAC                                        29
```

( 2 ) INFORMATION FOR SEQ ID NO:4:

( i ) SEQUENCE CHARACTERISTICS:
( A ) LENGTH: 26 BASE PAIRS
( B ) TYPE: NUCLEIC ACID
( C ) STRANDEDNESS: SINGLE
( D ) TOPOLOGY: LINEAR ( i i ) MOLECULE TYPE: Oligonucleotide ( x i ) SEQUENCE DESCRIPTION: SEQ ID NO:4:

GCGGCAAGCT TATTCTGTAG TATTGG    26

HUMAN TRANSCRIPTION FACTOR IIA

This invention relates to newly identified polynucleotides, polypeptides encoded by such polynucleotides, the use of such polynucleotides and polypeptides, as well as the production of such polynucleotides and polypeptides. More particularly, the polypeptide of the present invention is the small (γ) subunit of human transcription factor IIA, sometimes hereinafter referred to as "small subunit". The invention also relates to inhibiting the action of such polypeptides.

In prokaryotes, simply mixing purified RNA polymerase, a template carrying a promoter, nucleoside triphosphates, and appropriate buffer and salts is sufficient to obtain specific gene transcription in vitro beginning at the correct sites. Purified RNA polymerase from eukaryotes, however, initiates transcription very poorly and essentially at random. Accordingly, accessory factors are required for accurate initiation of transcription in eukaryotes. Some of these transcription factors are general factors required for initiation at all promoters, while others are gene-specific and are required only for certain promoters. Among the general factors is a protein called Transcription Factor IID "TFIID", which binds to a TATA sequence, wherein T represents thymidine and A represents adenosine, in promoters. Other general factors are also involved in the assembly of a multicomponent protein complex at the promoter.

In general, transcription factors are found to contain two functional domains, one for DNA-binding and one for transcriptional activation. These functions often reside within circumscribed structural domains that retain their function when removed from their natural context. The DNA-binding domains of transcription factors fall into several structural families based on their primary amino acid sequence.

In order to identify the specific nucleotides that control gene expression, regions of the gene flanking the coding region can be sequenced. Comparisons of these sequences reveal common patterns near the 5' and 3' ends of different genes. These are predicted to be important for proper transcription by RNA polymerase. The most common motif is the TATA sequence around 30 bp from the transcriptional start site. Other conserved sequences have been found roughly 50 to 100 bp upstream of the transcriptional start site.

Eukaryotic transcriptional activation requires the characterization of several multiprotein complexes, referred as general transcription factors and coactivators[1,2]. The heteromeric general transcription factor TFIIA binds directly to the TATA binding protein (TBP)[3,4] and has been implicated in the process of transcriptional activation[5-8]. The γ subunit of TFIIA binds weakly to the TATA binding protein, but strongly stabilized the binding of the large subunit of TFIIA (α β) to TBP. Recombinant human TFIIA is functional for the transcriptional activation mediated by at least three distinct activators. Both the α β and γ subunits are essential for activator dependent stimulation of TFIID by binding to promoter DNA, thus facilitating the first step in preinitiation complex formation. This demonstrates that TFIIA is an evolutionary conserved general transcription factor important for activator regulated transcription.

The interaction of TFIIA with the general transcription factor IID (TFIID) has been shown to be rate-limiting step in the transcriptional activation process[5]. TFIIA binds directly to TBP[3,4], the DNA binding subunit of the multiprotein TFIID complex[12]. TBP associated factors (TAFs)[12-14], which are essential for activated transcription, are also required for an activator-dependent stimulation of the TFIIA-TFIID-promoter complex[6]. While TFIIA has no known function in unregulated basal transcription[15], it has been postulated that TFIIA plays a role in preventing inhibitors of TFIID from repressing transcription[16-19].

A TFIIA homolog has been identified in yeast[9-10], and the genes encoding the two subunits are essential for viability[11]. Human TFIIA consists of three polypeptides (α, β, γ), but the two largest subunits are derived from a single gene which shares homology to the large subunit of yeast TFIIA[7,20,21]. Both the human and yeast protein bind to the evolutionary conserved domain of TBP[22] and stimulate transcription reconstituted with TFIID, but not TBP[17,19].

The polypeptide of the present invention has been putatively identified as the γ subunit of TFIIA. This identification has been made as a result of amino acid sequence homology.

In accordance with one aspect of the present invention, there is provided a novel mature polypeptide which is the small subunit of TFIIA, as well as fragments, analogs and derivatives thereof. The polypeptide of the present invention is of human origin.

In accordance with another aspect of the present invention, there are provided polynucleotides (DNA or RNA) which encode such polypeptide.

In accordance with yet a further aspect of the present invention, there is provided a process for producing such polypeptide by recombinant techniques.

In accordance with Met a further aspect of the present invention, there is provided a process for utilizing such polypeptide, or polynucleotide encoding such polypeptide for therapeutic purposes, for example, for regulating gene-specific or global transcription and to counteract repressors of the TFIID complex.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, to inhibit transcription of undesired cells, e.g., malignancies.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1(A) depicts the cDNA sequence (SEQ ID NO: 1) and corresponding deduced amino acid sequence (SEQ ID NO: 2) of the small subunit of human TFIIA. The small subunit polypeptide shown is the mature form of the polypeptide. Standard one-letter abbreviations for amino acids is used.

FIG. 1(B) illustrates a comparison of the amino acid composition of the human TFIIA small subunit and the yeast (TOA2) TFIIA small subunit.

FIG. 1(C) is a schematic diagram depicting the human TFIIA subunits. TFIIA is encoded by two genes, αβ and γ. The αβ protein is processed post-translationally into two polypeptides (α and β), approximately 35 and 19 kDa, respectively. Recombinant α and β polypeptides were designed with a breakpoint at amino acid residue 251, but this may not exactly correspond to the naturally occurring proteolytic cleavage site.

3

Figure 2A:
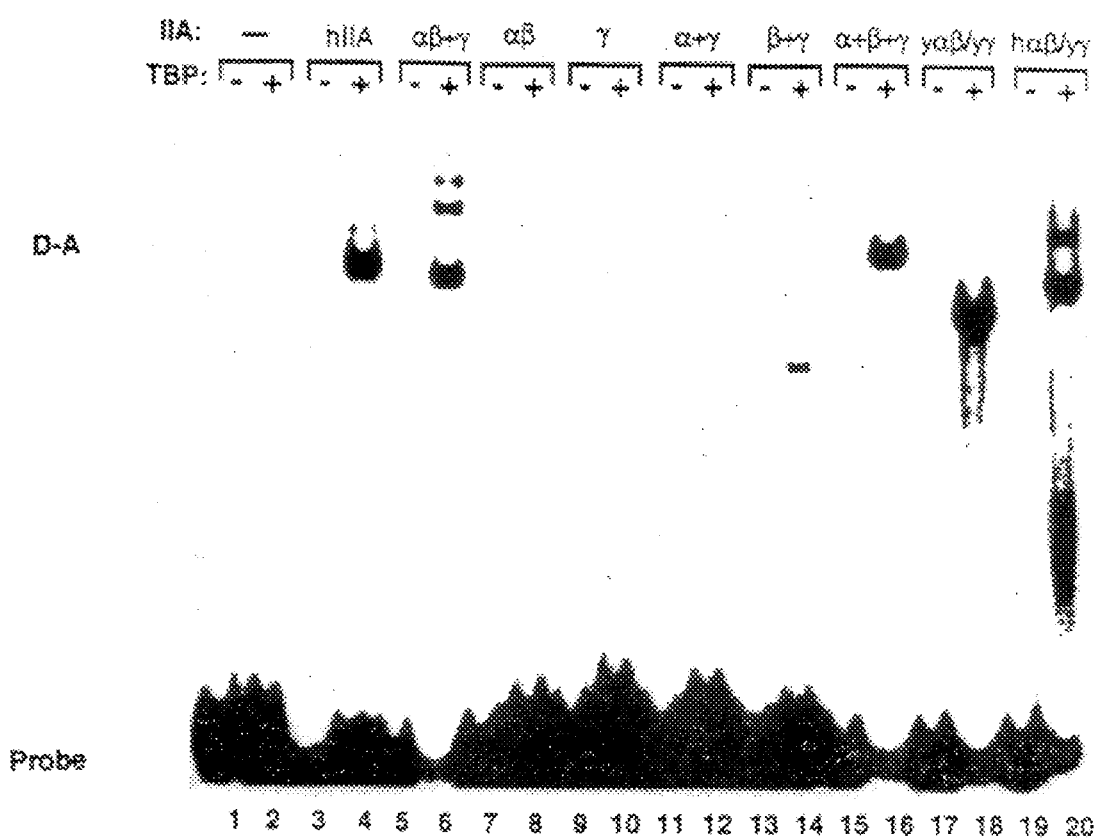

FIG. 2 illustrates the functional activity of recombinant human, yeast and heterologous TFIIA. FIG. 2(A) illustrates the formation of a D-A complex (resulting from the addition of TFIIA small subunit to TBP) bound to DNA detected by polyacrylamide gel EMSA (electrophoresis mobility shift assay). A 29 bp oligonucleotide probe containing the adenovirus E1B TATA element was incubated with various preparations of TFIIA in the absence (−) or presence (+) of 10 ng of yeast TBP as indicated above each lane. Approximately 50 ng of recombinant TFIIA was incubated in each reaction. Partially purified human TFIIA (hIIA, lanes 3,4), combinations of recombinant human subunits (αβ, α, β, γ, lanes 6–16), recombinant yeast αε with yeast γ (hαβ/yγ, lanes 19,20) are indicated above each lane.

Figure 2B:
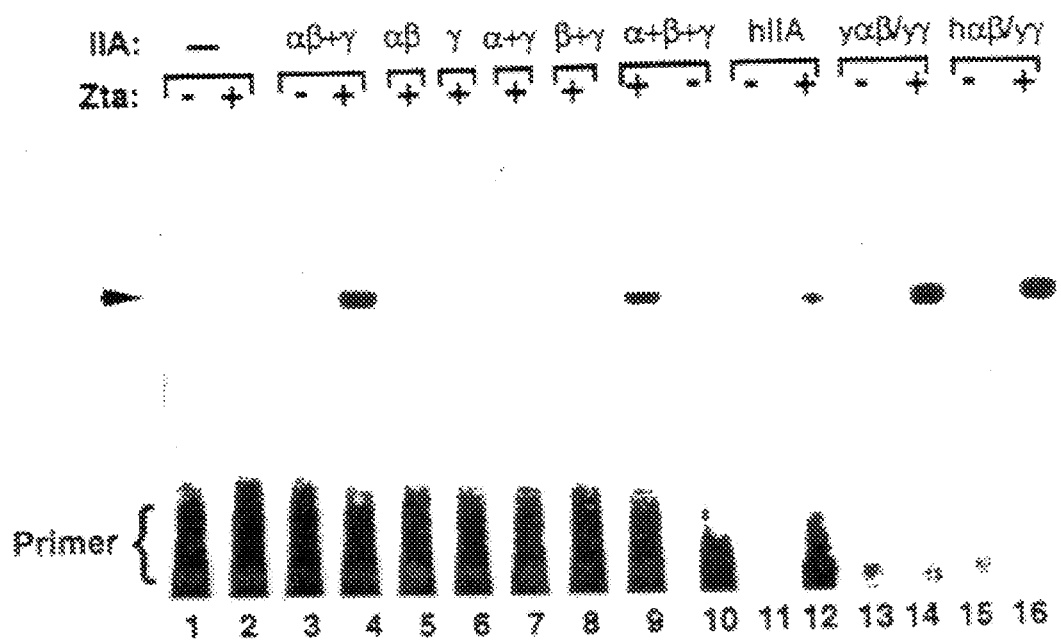

FIG. 2(B) illustrates the requirement of TFIIA activity in reconstitution of transcriptional activation by the Epstein-Barr virus encoded activator, Zta transcriptional activator. Transcription reactions were reconstituted with immunoaffinity purified TFIID, recombinant TFIIB, partially purified RNA polymerase II, TFIIE, TFIIF, and USA with (+) or without (−) Zta. Various TFIIA preparations were added to reactions as indicated above each lane. Arrow at the left indicates the correctly initiated transcript.

Figure 3A:
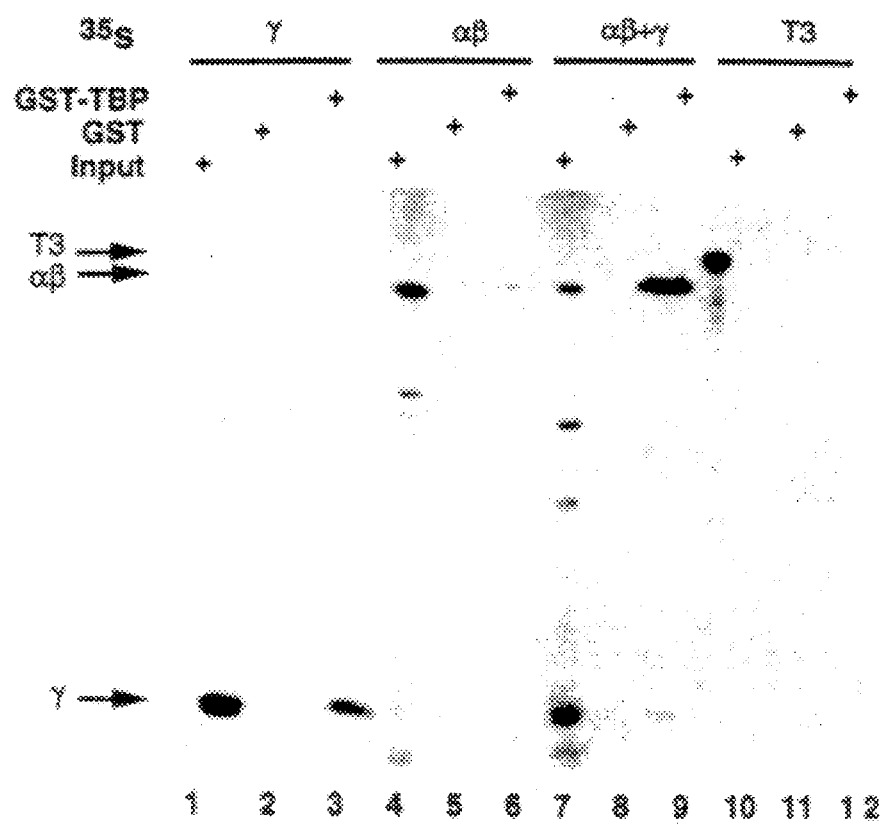

FIG. 3(A) illustrates the interaction of TFIIA subunits with TBP. $^{35}$S-labelled TFIIA γ (lanes 1–3), αβ (lanes 4–6), αβ+γ (lanes 7–9) or T3 luciferase control (lanes 10–12) proteins were incubated with GST (lanes 2, 5, 8, 11,) or GST-TBP (lanes 3, 6, 9, 12) immobilized on glutathione sepharose beads, as indicated above each lane. Lanes marked input (lanes 1, 4, 7, 10) represent approximately 2.5% of the reaction input.

Figure 3B:
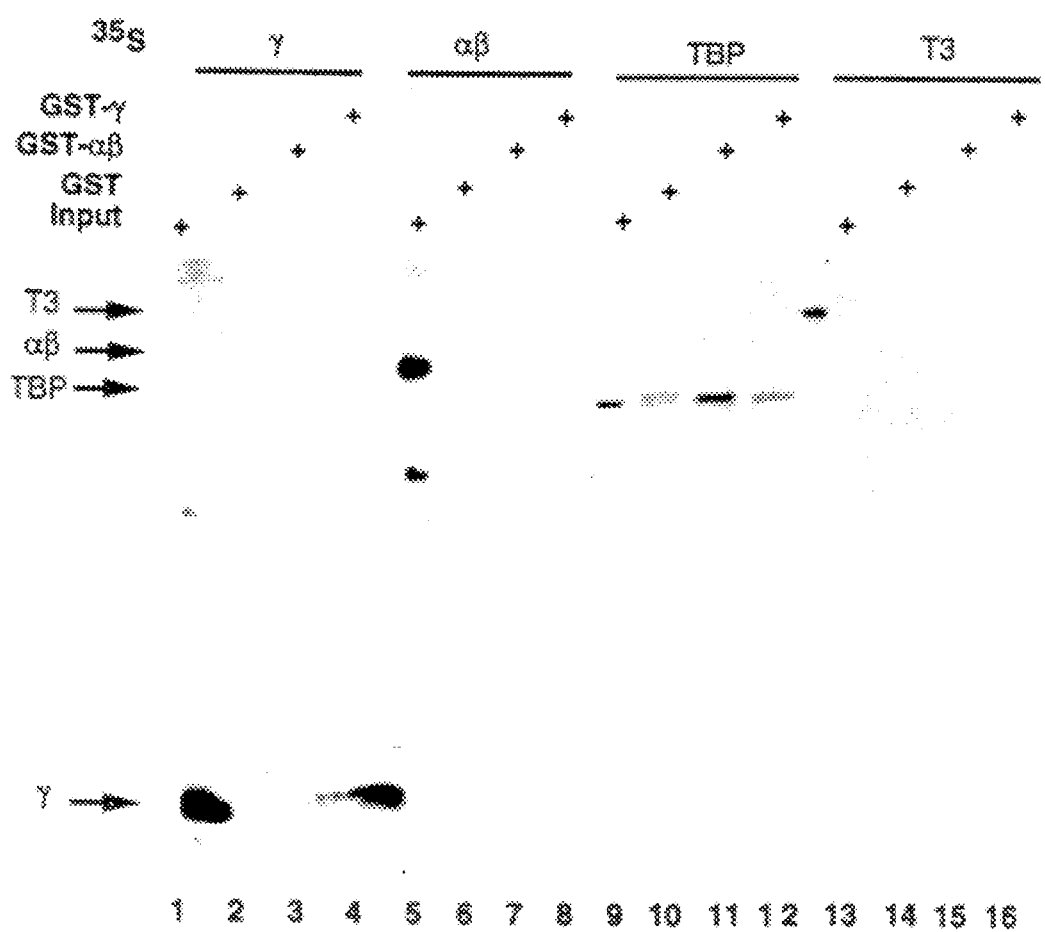

FIG. 3(B) illustrates that the interaction of TFIIA subunits reveals a strong homotypic binding of TFIIA γ. $^{35}$S labelled TFIIA γ (lanes 1–4), αβ (lanes 5–8), TBP (lanes 9–12) or T3luciferase (lanes 13–16) were incubated with GST (lanes 2, 6, 10, 14), GST-αβ (lanes 3, 7, 11, 15), or GST-γ (lanes 4, 8, 12, 16) fixed to gluthathione sepharose beads.

Figure 4A:
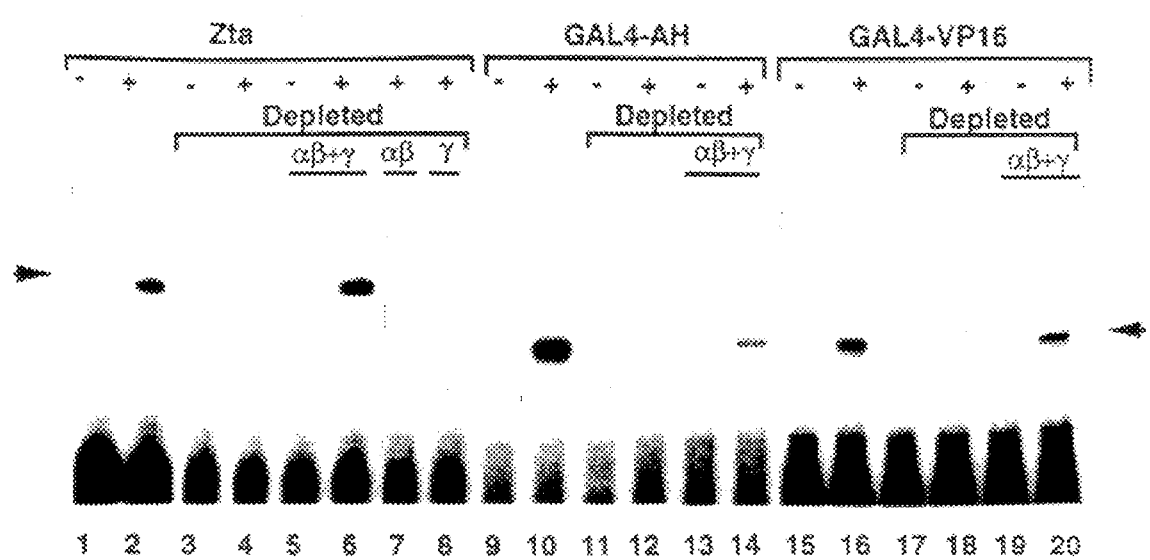

FIG. 4(A) illustrates that recombinant TFIIA restores the ability of three distinct activation domains to function in TFIIA depleted nuclear extracts. The transcriptional activator proteins Zta (lanes 2, 4, 6, 7, 8, 9), GAL4-AH (lanes 10, 12, 14) or VP16 (lanes 16, 18, 20) were incubated with untreated HeLa cell nuclear extract (lanes 1, 2, 9, 10, 15, 16) or with TFIIA depleted HeLa cell nuclear extracts (lanes 3–9, 11–14, 17–20) in in vitro transcription reactions. 50 ng of recombinant TFIIA αβ+γ (lanes 5, 6, 13, 14, 19, 20), TFIIA αβ (lane 7), or TFIIA γ (lane 8) was supplemented to depleted extracts. Correctly initiated primer extension products for Zta and GAL4 templates are indicated by the arrows at the left and right, respectively.

Figure 4B:
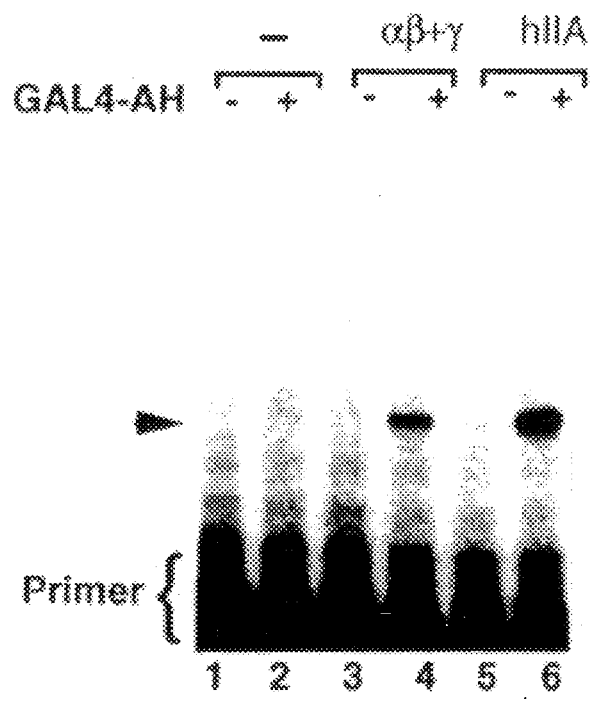

FIG. 4(B) illustrates the requirement for TFIIA in the reconstitution of transcriptional activation by an acidic activator with partially purified general transcription factors. Transcription reactions were essentially the same as those described for FIG. 2(B), except that the GAL-AH activator and the G$_5$E1BTCAT template were used.

Figure 4C:
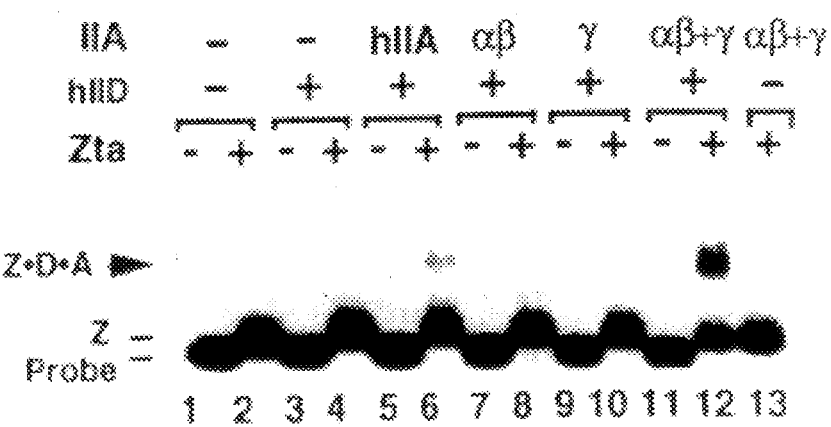

FIG. 4(C) shows that recombinant TFIIA promotes an activator and TAF dependent TFIID promoter complex. Mg agarose gel EMSA of DNA binding reactions with immunopurified TFIID (lanes 3–12), Zta (even lanes, and 13), and a 250 bp probe derived from the Z7E4TCAT promoter. Zta (20 ng), recombinant TFIIA (50 ng), and 0.1 footprinting unit of TFIID were incubated with approximately 1 fmole of radiolabelled promoter DNA for 15 minutes at room temperature.

Sequencing inaccuracies are a common problem when attempting to determine polynucleotide sequences.

4

Accordingly, the sequence of FIG. 1A is based on several sequencing runs and the sequencing accuracy is considered to be at least 97%.

In accordance with an aspect of the present invention, there is provided an isolated nucleic acid (polynucleotide) which encodes for the mature polypeptide having the deduced amino acid sequence of FIG. 1A or for the mature polypeptide encoded by the cDNA of the clone deposited as ATCC Deposit No. 75809 on Jun. 10, 1994.

The ATCC number referred to above is directed to a biological deposit with the ATCC, 12301 Parklawn Drive, Rockville, Md. 20852. The strain is being maintained under the terms of the Budapest Treaty and will be made available to a patent office signatory to the Budapest Treaty.

The polynucleotide of this invention was discovered in a T-cell library. It is structurally related to the small subunit of yeast (TOA2). It contains an open reading frame encoding a protein of 109 amino acid residues. The protein exhibits the highest degree of homology to yeast TOA2 with 40% identity and 50% similarity over the entire amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1A or that of the deposited clone or may be a different coding sequence which coding sequence, as a result of the redundancy or degeneracy of the genetic code, encodes the same mature polypeptide as the DNA of FIG. 1A or the deposited cDNA.

The polynucleotide which encodes for the mature polypeptide of FIG. 1A or for the mature polypeptide encoded by the deposited cDNA includes only the coding sequence for the mature polypeptide since the polypeptide is a nuclear protein which is not excreted to the outside of the cell.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1A or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1A or the same mature polypeptide encoded by the cDNA of the deposited clone as well as variants of such polynucleotides which variants encode for a fragment, derivative or analog of the polypeptide of FIG. 1A or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1A or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides . As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1A or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of Skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to the small subunit of TFIIA polypeptide which has the deduced amino acid sequence of FIG. 1A or which has the amino acid sequence encoded by the deposited cDNA, as well as fragments, analogs and derivatives of such polypeptide.

The terms "fragment," "derivative" and "analog" when referring to the polypeptide of FIG. 1A or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1A or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, which are employed for purification of the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the TFIIA genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transforman appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calciumphosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The TFIIA small subunit polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

While Applicant does not wish to limit the scientific reasoning in the present invention to any particular theory, the following procedures are illustrations of the functional aspects of TFIIA as a whole and the small ($\gamma$) subunit, in particular.

TFIIA activity was first assayed for the stabilization of TBP binding to a TATA box containing oligonucleotide probe in polyacrylamide gel EMSA (FIG. 2A). In the absence of TFIIA, yeast TBP does not form a stable complex with a TATA box containing oligonucleotide (lane 2). Addition of partially purified human TFIIA (hIIA) to TBP resulted in the formation of a stable complex (D-A) (lane 4). Recombinant $\alpha\beta+\gamma$ also produced a stable D-A complex (lane 6). TBP failed to form the stable D-A complex when the $\alpha\beta$ or $\gamma$ subunit was added individually (lanes 8 and 10). Since natural TFIIA occurs as three polypeptides, the $\alpha\beta$ protein was expressed as two independent subunits (FIG. 1C). The $\alpha+\gamma$ had no effect (lane 12), while $\beta+\gamma$ had a small effect (lane 14) on TBP binding. In contrast, the combination of $\alpha$, $\beta$ and $\gamma$ subunits ($\alpha\beta+\gamma$) resulted in strong stimulation of TBP binding, while electrophoretic mobility was very similar to the native human TFIIA protein (lane 16). In addition, the yeast $\gamma$ subunit could also form a stable D-A complex when mixed with the human $\alpha\beta$ Subunit, demonstrating the interaction between the $\alpha\beta$ and $\gamma$ subunits is evolutionarily conserved (lane 20). The electrophoretic mobility of the D-A complex was influenced by the different $\alpha\beta\gamma$ forms of TFIIA, suggesting that TFIIA is retained in the bound complexes.

The various TFIIA complexes were analyzed for their ability to support transcriptional activation in reactions reconstituted with partially purified general transcription factors, the coactivator USA[25], and the Epstein-Barr virus encoded activator, Zta[6]. The $\gamma$ subunit was essential for transcriptional activation, and the $\alpha$ and $\beta$ subunit could be supplemented as either a single $\alpha\beta$ polypeptide, or as two distinct polypeptides ($\alpha+\beta$) (FIG. 2B). In all cases, the formation of the D-A complex in EMSA correlated with the ability of TFIIA to support transcriptional activation by Zta.

Radio labelled $\alpha\beta$, $\gamma$ or $\alpha\beta+\gamma$ proteins were tested for their ability to interact with glutathione-S-transferase (GST) or GST-TBP fusion proteins immobilized on glutathione agarose (FIG. 3A). The $\gamma$ subunit bound weakly, but specifically to GST-TBP (lane 3), as did the $\alpha\beta$ subunit (lane 6). Significantly, the combination of the $\alpha\beta+\gamma$ subunits markedly increased the binding to GST-TBP (lane 9). The ability of radiolabelled TBP to bind to GST-$\gamma$ and GST-$\alpha\beta$ was also examined (FIG. 3B). TBP bound to GST-$\gamma$ protein, but failed to interact with the GST-$\gamma$ protein (FIG. 3B, lanes 11 and 12). The discrepancy of the binding of $\gamma$ to TBP may be a partial result of the steric hindrance of GST fused to the amino terminus of $\gamma$. Although both $\alpha\beta$ and $\gamma$ are capable of making direct contact with TBP, the heterodimer clearly binds with higher affinity.

The interaction of $\gamma$ with the $\alpha\beta$ polypeptides was also examined by the GST-fusion protein binding assay. Radiolabelled $\gamma$, $\alpha\beta$, or T3 control were incubated with GST-$\gamma$, GST-$\alpha\beta$, or GST alone (FIG. 3B). As expected, the $\alpha\beta$ subunit bound to GST-$\gamma$ and the $\gamma$ subunit bound to GST-$\alpha\beta$. The $\gamma$ subunit also bound strongly to GST-$\gamma$, while $\alpha\beta$ did not bind GST-$\alpha\beta$, suggesting that a homotypic association of the $\gamma$ subunit contributes to the oligomerization state of TFIIA. The T3 control protein did not interact with any of the GST proteins tested.

To determine whether TFIIA was required for transcriptional activation by activators distinct from Zta, the need for TFIIA by the acidic activator GAL4-AH[26] and the herpes virus derived activator GAL4-VP16[27] was examined. Zta is not an acidic activator, like AH and shares no obvious homology to the VP16 activation modules. TFIIA depleted HeLa cell nuclear extracts were prepared by serial passage over nickel agarose, which binds specifically to the $\alpha\beta$ subunit of TFIIA.[7,20] Addition of Zta to the depleted extract failed to produce significant transcription levels (FIG. 3A, lane 4). Addition of TFIIA $\alpha\beta+\gamma$ subunits restored activation of the depleted extracts to levels observed in the undepleted extract (compare lanes 2 and 6). The $\alpha\beta$ or $\gamma$ subunit alone failed to restore Zta activation in these depleted extracts indicating that both subunits were equally depleted by the nickel agarose. Similarly, GAL4-AH (lanes 9–14) and GAL4-VP16 (lanes 15–20) did not function in the TFIIA depleted extracts. Addition of recombinant $\alpha\beta+\gamma$ subunits restored activator dependent transcription for all three distinct activators. GAL4-AH was also shown to require TFIIA in reconstituted transcription assays (FIG. 4B) as did Zta (FIG. 2B). These results indicate that distinct activation domains require TFIIA for activated transcription in both crude nuclear extracts, as well as in more purified reconstitution systems.

Partially purified TFIIA is required for an activation domain stimulation of TFIID binding to promoter DNA.[6] Using Mg agarose gel EMSA, it was found that recombinant TFIIA substitutes for the partially purified TFIIA in this function (FIG. 4C). In the absence of TFIIA, Zta does not stimulate the formation of a TFIID-DNA complex (FIG. 4C, lane 4). However, the addition of partially purified TFIIA (lane 6) or $\alpha\beta+\gamma$ (lane 12), but not $\alpha\beta$ or $\gamma$ alone (lanes 7–10) allows Zta stimulation of TFIID binding to the promoter DNA. These results demonstrate that TFIIA mediates an interaction between activators and TFIID, which result in the increase affinity of TFIID for promoter DNA.

The isolation of the γ subunit of human TFIIA has allowed testing for the requirement for highly purified TFIIA in the reconstitution of activated transcription in vitro. Several distinct activation domains require TFIIA for their ability to function. The recombinant human γ subunit, has also been shown to be functionally interchangeable in in vitro transcription and TBP binding assays.

The TFIIA small subunit polypeptide may be used to prevent inhibitors of TFIID from repressing transcription, this is useful where a particular gene product is desired and is not being produced at the desired levels due to the inhibition of the TFIID complex.

Most importantly, the TFIIA small subunit polypeptide may be used to regulate transcription globally or in a gene-specific manner, to obtain desired concentrations of particular proteins. For example, in the case of a malignancy, the TFIIA small subunit may be repressed to prevent transcription and in the case where a protein is desired, for example growth hormone, the TFIIA small subunit may enhance transcription and the production of the gene product.

The polypeptide of the present invention is also useful for identifying other molecules which have similar biological activity. An example of a screen for this is isolating the coding region of the small subunit of the TFIIA gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides a method of screening compounds to identify those which enhance (agonists) or block (antagonists) interaction of the small subunit of TFIIA with TFIID. An agonist is a compound which increases the natural biological function of the small subunit of TFIIA, while antagonists eliminate such functions. As an example, purified RNA polymerase, a template carrying a promoter, nucleoside triphosphates and appropriate buffer and salts may be mixed with TFIIA and TFIID in the presence of the compound under conditions where transcription would normally take place. The ability of the compound to enhance or block the binding of TFIIA to the template DNA could then be determined by measuring the level of transcription product.

Alternatively, the assay may be a cell-based assay wherein a TFIIA-inducible promoter drives the expression of a marker gene. TFIIA and the compound to be screened would then be added to measure the level of production of the marker gene. Additionally, this cell-based assay could be used in tandem with the binding assay to determine if the effects on transcription are specific to TFIIA agonism or antagonism.

Potential antagonists include an antibody, or in some cases, an oligonucleotide, which binds to the small subunit of TFIIA. Alternatively, a potential antagonist may be a closely related protein which binds to the TBP protein of the TFIID complex but do not initiate transcription. An example of such a closely related protein is a negative dominant mutant, wherein one the two subunits of TFIIA are mutated and do not retain function. The negative dominant mutant, however, still recognizes substrate but does not initiate transcription.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the TFIIA small subunit. The antisense RNA oligonucleotide hybridizes to the mRNA in vivo and blocks translation of the mRNA molecule into the TFIIA small subunit (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the small subunit of TFIIA.

Potential antagonists include a small molecule which binds to and occupies the active site of the polypeptide such that TFIIA is unable to activate TFIID and initiate transcription. Examples of small molecules include but are not limited to small peptides or peptide-like molecules.

The antagonists may be employed to inhibit the transcription of undesired polypeptides. For example, where a particular polypeptide leads to an undesired condition the antagonists mentioned above may be used to prevent transcription of that polypeptide. An example of this is the transcription and differentiation of cancerous cells. The antagonists may be employed in a composition with a pharmaceutically acceptable carrier, e.g., as hereinafter described.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The small subunit polypeptide of TFIIA and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Fragments of the full length TFIIA small subunit gene may be used as a hybridization probe for a cDNA library to isolate the full length TFIIA small subunit gene and to isolate other genes which have a high sequence similarity to the gene. Probes of this type can be, for example, 30, 40, 50 75, 90, 100 or 150 bases. Preferably, however, the probes have between 30 and 50 base pairs. The probe may also be used to identify a cDNA clone corresponding to a full length transcript and a genomic clone or clones that contain the complete gene including regulator and promotor regions, exons, and introns. The probe may be labelled, for example, by radioactivity to facilitate identification of hypbridization.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, INC., pp. 77–96).

Techniques described for the production of single chain antibodies (U.S. Pat. No. 4,946,778) can be adapted to produce single chain antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel (or an agarose gel) to isolate the desired fragment, as described in Sambrook et al., Molecular Cloning: A laboratory Manual, Second Edition, Cold Spring Harbor, N.Y. (1989).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of the Small TFIIA Subunit

The DNA sequence encoding for the small TFIIA subunit, ATCC #75809, is initially amplified using PCR oligonucleotide primers corresponding to the 5' and sequences of the processed TFIIA subunit protein and the vector sequences 3' to the small subunit of TFIIA gene. Additional nucleotides corresponding to the small subunit of TFIIA were added to the 5' and 3' sequences respectively. In the case of the γ subunit, the 5' oligonucleotide primer has the sequence 5'GCGGCGGATCCATGGCATATCAGGTATAC3' (SEQ ID NO: 3) contains a Bam HI restriction enzyme site followed by 18 nucleotides of the small subunit of TFIIA (underlined) coding sequence starting from the presumed terminal amino acid of the processed protein codon. The 3' sequence 5'GCGGCAAGCTTATTCTGTAGTATTGG3' (SEQ ID NO: 4) contains complementary sequences to HindIII site and is followed by 13 nucleotides of the small subunit of TFIIA (underlined). The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9was then digested with Bam HI and Hind III. The amplified sequences were ligated into pQE-9 and were inserted in frame with 6 His residues fused to the amino terminus. The ligation mixture was then used to transform E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis.

Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized TFIIA subunits was purified from this solution by chromatography on a Nickel-Agarose column under conditions that allow for tight binding by proteins containing the 6-His tag (Hochuli, E. et al., J. Chromatography 411:177–184 (1984)). The small subunit of TFIIA (95% pure) was eluted from the column in 6 molar guanidine HCl pH 5.0 and were allowed to renature by themselves of in stoichiometric combination with the specified protein (see FIG. 2). Gel Mobility Shift assays were used to separate the transcription products as they appear in the Figure.

EXAMPLE 2

Interaction of Small Subunit of TFIIA with qlutathione-S-transferase or GST-TBP Fusion Proteins Bacterial extracts of GST or GST fusion proteins were incubated with glutathione sepharose-4B beads (6–9 μg of GST-fusion protein/20 μl of beads) with shaking at 4° C. After 2 hours the beads were washed with 50 column volumes of cold buffer A (20 mM NaH$_2$PO$_4$ (pH 7.0) 150 mM NaCl, 1 mM DTT, 1 mM PMSF). Washed beads (20 μl) were then incubated with reticulocyte lysates containing 2×10$^4$ cpm of $^{35}$S labelled protein in 300 μl of protein binding buffer (PBB) for 1 hour at room temperature. PBB contained 20 mM Hepes (pH 7.9), 20% glycerol, 0.5 mM EDTA, 60 mM KCl, 5 mM MgCl2, 0.1% NP40, and 5 mM β-mercaptoethanol. The beads were subsequently washed 4 times in PBB and labeled proteins were eluted with 1M KCl. Samples were analyzed on 15% SDS polyacrylamide gels, enhanced with NaSalycilate, and visualized by autoradiography.

EXAMPLE 3

Transcription Reactions Utilizing TFIIA

Transcription reactions contained 100 ng of the Z7E4TCAT[29] or G5E1BTCAT[26] template, approximately 200 ng of activator protein, and 40 μg of nuclear extract in a 50 μl final reaction volume. TFIIA depleted nuclear extracts were prepared by dialyzing HeLa cell nuclear extract in buffer D in 20 mM Hepes (pH 7.9), 20% glycerol, 5 mM β-mercaptoethanol, 1 mM PMSF, containing 500 mM KCl, followed by two sequential incubations with Nickel agarose beads (150 ul packed beads/1 mg of nuclear extract) for 20 minutes at 4° C. rotating. Depleted extracts were dialyzed into D buffer containing 100 mM KCl. The reconstituted transcription reactions and the Mg agarose EMSA were described previously[6].

Numerous modifications and variations of the present invention are possible in light of the above teachings and, therefore, within the scope of the appended claims, the invention may be practiced otherwise than as particularly described.

REFERENCES:

1. Tjian, R. and Maniatis, T. Cell 77, 5–8 (1994).
2. Zawel, L. and Reinberg, D. Prog. Nucl. Acids. Res. Mol. Biol. 44, 67–108 (1993).
3. Buratowski, S. Hahn, S. Guarente, L., and Sharp, P. A. Cell 56, 549–561 (1989).
4. Maldonado, E., Ha, I., Cortes, P., Weiss, L., and Reinberg, D. Mol. Cell. Biol., 12, 6335–6347 (1990).
5. Wang, W., Gralla, J. D., and Carey, M. Genes and Dev. 6, 1716–1727 (1992).
6. Lieberman, P. and Berk, A., Genes and Dev., 8:995–1006 (1994).
7. Ma, D., Watanabe, H., Memelstein, F., Admon, A., Oguri, K., Xiaoqing, S., Wada, T., Imai, T., Shiroya, T., Reinberg, D., and Handa, H. Genes Dev. 7, 2246–2257 (1993).
8. Chi, T., and Carey, M. Mol. Cell. Biol., 13, 7045–7055 (1993).
9. Hahn, S., Buratowski, S., Sharp, P., and Guarente, L., EMBO J., 8, 3379–3382 (1989).
10. Ranish, J. A. and Hahn, S. J. Biol. Chem. 266, 19320–19327 (1991).
11. Ranish, J. A., Lane, W. S. and Hahn, S. Science 255, 1127–1129 (1992).
12. Hernandez, N. Genes Dev. 7, 1291–1308 (1993).
13. Dynlacht, B. D., Hoey,. T., and Tjian, R. Cell 66, 563–576 (1991).
14. Tanese, N., Pugh, B. F., and Tjian, R. Genes and Dev. 5, 2212–2224 (1991).
15. Tyree, C. M., George, C. P. Lira-De Vito, L., Wampler, S. Dahmus, M. E., Zawel, L., and Kadonaga, J. T. 7, 1254–1265 (1993).
16. Roeder, R. G. Trends Biochem. Sci. 16, 402–408 (1991).
17. Cortes, P., Flores, O., and Reinberg, D. Mol. Cell. Biol. 12, 412–421 (1992).
18. Merino, A., Madden, K., Lane, W. S., Champoux, J., and Reinberg, D. 1993. Nature 365, 327–332 (1993).
19. Drapkin, R. Merino, A. and Reinberg, D. Cur. Opin. Cell. Biol., 5, 469–476 (1993).
20. DeJong, J. and Roeder, R. Genes and Dev. 7, 2220–2234 (1993).
21. Yokomuri, K., Admon, A., Goodrich, J. A., Chen, J. L., and Tjian, R. Genes Dev. 7, 2235–2245 (1993).
22. Buratowski, S. and Zhou, H. Science 255:1130–1132 (1992).
23. Adams, M. D. et al., Science 252, 1651 (1991).
24. Adams, M. D., et al., Nature 355:632–634 (1992).
25. Meisterernst, M., Roy, A. L., Lieu, H.M., and Roeder, R. G. Cell 66, 981–993 (1991).
26. Lin, Y. S., Carey, M., Ptashne, M., and Green, M. Cell 54, 659–664 (1988).
27. Chasman, D. I., Leatherwood, J., Carey, M., Ptashne, M., and Korngerg, R. Mol. Cell. Biol. 9, 4746–4749 (1989).
28. Kao, C. C., Lieberman, P. M., Schmidt, M. C., Zhou, Q., Pei, M. R., and Berk, A. Science 248, 1646–1650 (1990).
29. Carey, M., Kolman, J., Katx, D. A., Gradoville, L., Barberis, L., and Miller, G. J. Virol. 66, 4803–4813 (1992).

Zhou, Q., Lieberman, P. M., Boyer, T. G. and Berk, A. J. Genes Dev. 6, 1964–1974 (1992).

What is claimed is:

1. An isolated polynucleotide comprising a polynucleotide member selected from the group consisting of:
   (a) a polynucleotide having a sequence with at least 95% identity to a polynucleotide coding sequence which encodes amino acids 2 to 109 of SEQ ID NO: 2; and
   (b) the complement of the polynucleotide of (a).

2. The isolated polynucleotide of claim 1 wherein said member is the polynucleotide of (a).

3. The isolated polynucleotide of claims 1 wherein said polynucleotide is the polynucleotide of (a) and has a polynucleotide coding sequence which encodes amino acids 1 to 109 of SEQ ID NO: 2.

4. The isolated polynucleotide of claim 1 wherein said polynucleotide is identical to a polynucleotide coding sequence which encodes amino acids 2 to 109 of SEQ ID NO: 2.

5. The isolated polynucleotide of claim 1, wherein the polynucleotide is DNA.

6. The isolated polynucleotide of claim 1 wherein said polynucleotide is identical to a polynucleotide coding sequence which encodes amino acids 1 to 109 of SEQ ID NO: 2.

7. The isolated polynucleotide of claim 1, wherein said polynucleotide is RNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2, wherein said polynucleotide is DNA.

11. A method for producing a polypeptide comprising expressing from the recombinant cell of claim 10 the polypeptide encoded by said polynucleotide.

12. A process for producing a polypeptide comprising:
expressing from a recombinant cell containing the polynucleotide of claim 4 the polypeptide encoded by said polynucleotide.

13. A process for producing a polypeptide comprising:
expressing from a recombinant cell containing the polynucleotide of claim 6 the polypeptide encoded by said polynucleotide.

14. The isolated polynucleotide of claim 2 wherein the polynucleotide of (a) consists of the sequence of nucleotides 193 to 519 of SEQ ID NO: 1.

15. The isolated polynucleotide of claim 2 wherein the polynucleotide of (a) consists of the sequence of nucleotides from 190 to 519 of SEQ ID NO: 1.

16. The isolated polynucleotide of claim 1 comprising the nucleotide sequence of SEQ ID NO: 1.

17. An isolated polynucleotide comprising a polynucleotide member selected from the group consisting of:
   (a) a polynucleotide having a sequence with at least 95% identity to a polynucleotide coding sequence which encodes the same mature polypeptide encoded by the human cDNA in ATCC Deposit No. 75809
   (b) the complement of the polynucleotide of (a).

18. The isolated polynucleotide of claim 17, wherein the member is (a).

19. The isolated polynucleotide of claim 17, wherein said polynucleotide comprises DNA identical to the coding portion of the human cDNA in ATCC Deposit No. 75809 which encodes a mature polypeptide.

20. An isolated polypeptide comprising:
a mature polypeptide having an amino acid sequence encoded by a polynucleotide which, is at least 95% identical to the polynucleotide of claim 4.

21. The isolated polypeptide of claim 20, comprising amino acids 2 to 109 of SEQ ID NO: 2.

22. The isolated polypeptide of claim 20 comprising amino acids 1 to 109 of SEQ ID NO: 2.

23. An isolated polypeptide comprising:
the mature polypeptide encoded by a polynucleotide which is at least 95% identical to the human cDNA contained in ATCC Deposit No. 75809.

24. The isolated polypeptide of claim 23 comprising the mature polypeptide encoded by the human cDNA in ATCC Deposit No. 75809.

* * * * *